(12) United States Patent
Kim et al.

(10) Patent No.: US 10,933,030 B2
(45) Date of Patent: Mar. 2, 2021

(54) USE OF PAEONOL FOR INHIBITING ANGIOGENESIS OR FOR ENHANCING RADIOSENSITIZATION

(75) Inventors: Min-Young Kim, Taejon (KR); Hee-Suk Lee, Seoul (KR); Ki-Hwan Bae, Taejon (KR); Yeon-Sook Yun, Seoul (KR); Jie-Young Song, Goyang-si (KR); Young-Soo Han, Buchon-si (KR)

(73) Assignee: ANGIOLAB, INC., Daejon (KR)

( * ) Notice: Subject to any disclaimer, the term of this patent is extended or adjusted under 35 U.S.C. 154(b) by 0 days.

(21) Appl. No.: 11/913,769

(22) PCT Filed: May 4, 2006

(86) PCT No.: PCT/KR2006/001702
§ 371 (c)(1),
(2), (4) Date: Nov. 6, 2007

(87) PCT Pub. No.: WO2006/121263
PCT Pub. Date: Nov. 16, 2006

(65) Prior Publication Data
US 2008/0194700 A1    Aug. 14, 2008

(30) Foreign Application Priority Data

May 6, 2005 (KR) .................. 10-2005-0038014
May 6, 2005 (KR) .................. 10-2005-0038015

(51) Int. Cl.
| A61K 31/05 | (2006.01) |
| A61K 41/00 | (2020.01) |
| A61P 35/00 | (2006.01) |
| A61K 35/00 | (2006.01) |

(52) U.S. Cl.
CPC .............. *A61K 31/05* (2013.01); *A61K 35/00* (2013.01); *A61K 41/0038* (2013.01)

(58) Field of Classification Search
CPC ...... A61K 31/05; A61K 41/0038; A61P 35/00
See application file for complete search history.

(56) References Cited

U.S. PATENT DOCUMENTS

| 5,652,255 | A * | 7/1997 | Adams et al. ............ 514/398 |
| 6,569,468 | B2 | 5/2003 | Xiao |
| 2006/0110468 | A1 | 5/2006 | Liu |
| 2019/0329069 | A1 * | 10/2019 | Blankenbecler ..... A61N 5/1038 |

FOREIGN PATENT DOCUMENTS

| CN | 1163763 A | 11/1997 |
| CN | 1205232 A | 1/1999 |
| CN | 1045527 C | 10/1999 |
| CN | 1054748 C | 7/2000 |
| CN | 1142338 A | 2/2003 |
| GB | 2424833 B | 12/2008 |
| WO | WO 9522323 A1 * | 8/1995 ............ A61K 31/12 |
| WO | 02/32438 A1 | 4/2002 |

OTHER PUBLICATIONS

Chang et al (Anticancer Research Athens, Mar.-Apr. 1994; 14(2A): 501-6).*
"Principles of Cancer Therapy." Cecil's Textbook of Medicine (Twenty-First Edition, vol. 1). W.B. Saunders Company, 2000. pp. 1060-1074.*
Chang et al. Inhibitory effects of phenolics on xanthine oxidase. Anticancer Research 14: 501-506, 1994.*
National Cancer Institute. Understanding Cancer Series: What is Tumor Angiogenesis. Available Jan. 28, 2005. http://www.cancer.gov/cancertopics/understandingcancer/angiogenesis/Slide3.*
Rosenberg. Immunotherapy and Gene Therapy of Cancer. Cancer Research, 51, 5074s-5079s, 1991.*
Brittanica Academic Edition. Definition of cervix. 2012. Electronic Resource. [http://www.britannica.com/EBchecked/topic/620581/uterine-cervix].*
Guoping et al. Zhongguo Yaolixue Tongbao, 2003, 19(2), 160-162. English language abstract.*
Lawrence et al., Semin. Rad. Oncol. 13(1), 13-21 (2003).*
Chung, "Paeonol promotion of DNA adduct formation and arylamines N-acetyltransferase activity in human colon tumour cells," Food and Chemical Toxicology, 37:327-334, 1999.

* cited by examiner

*Primary Examiner* — Theodore R. Howell
(74) *Attorney, Agent, or Firm* — Nixon & Vanderhye P.C.

(57) ABSTRACT

The present invention relates to a composition comprising paeonol of formula (I) or a pharmaceutically acceptable salt thereof as an active ingredient for inhibiting angiogenesis, or for enhancing radiosensitization. The present invention also relates to novel use of paeonol of formula (I) or a pharmaceutically acceptable salt thereof for the manufacture of a composition for inhibiting angiogenesis, or for the manufacture of a composition for enhancing radiosensitization. Also, the present invention relates to a method for inhibiting angiogenesis which comprises administrating to a subject in need thereof an effective amount of paeonol of formula (I) or a pharmaceutically acceptable salt thereof, or a method for enhancing radiosensitization which comprises administrating an effective amount of paeonol of formula (I) or pharmaceutically acceptable salts thereof to a subject in need of radiotherapy.

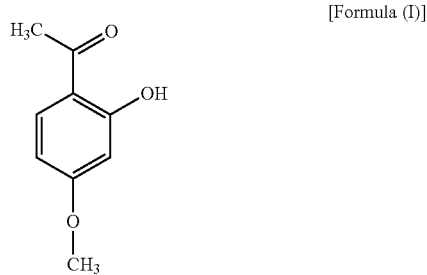

[Formula (I)]

5 Claims, 6 Drawing Sheets

[Fig. 1]
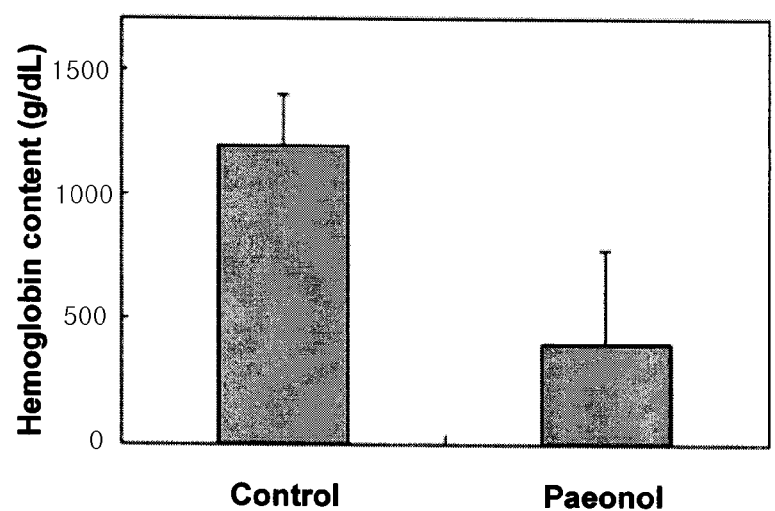
[Fig. 2]
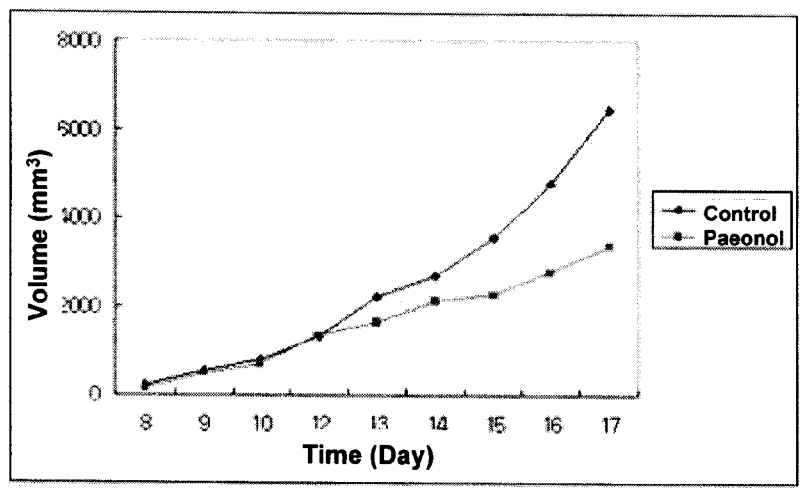

[Fig. 3]
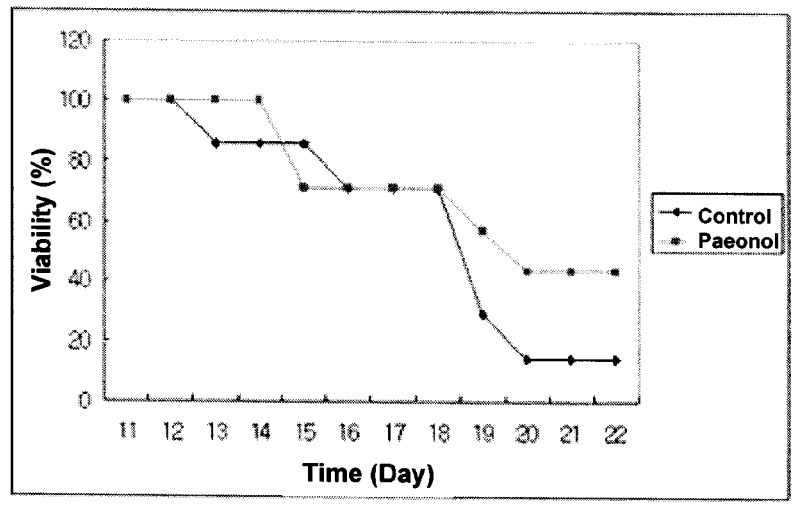
[Fig. 4]
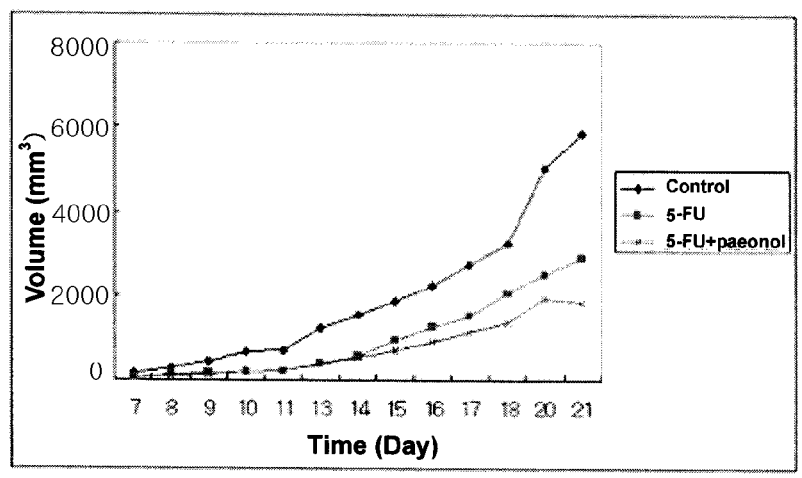

[Fig. 5]
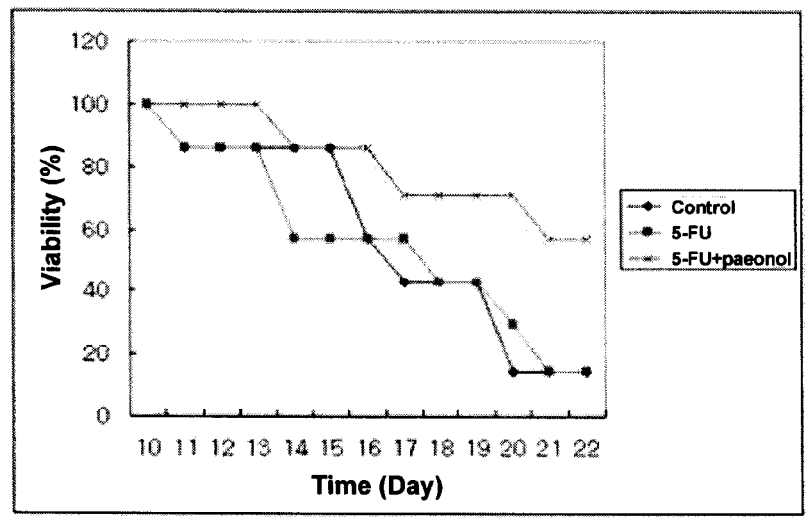
[Fig. 6]
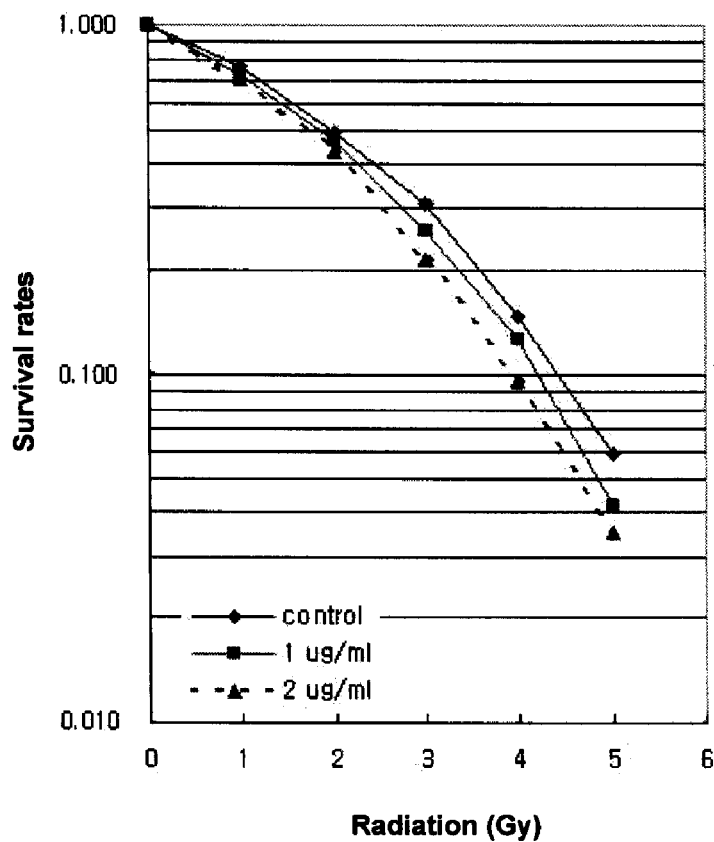

[Fig. 7]
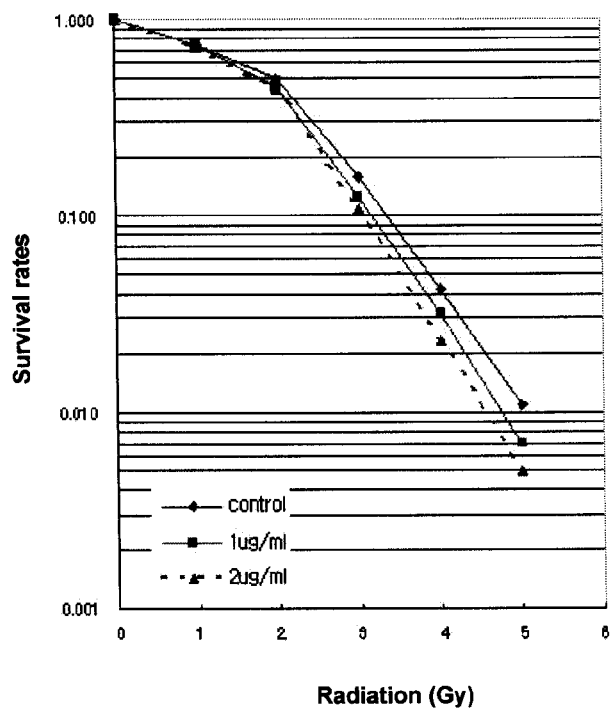
[Fig. 8]
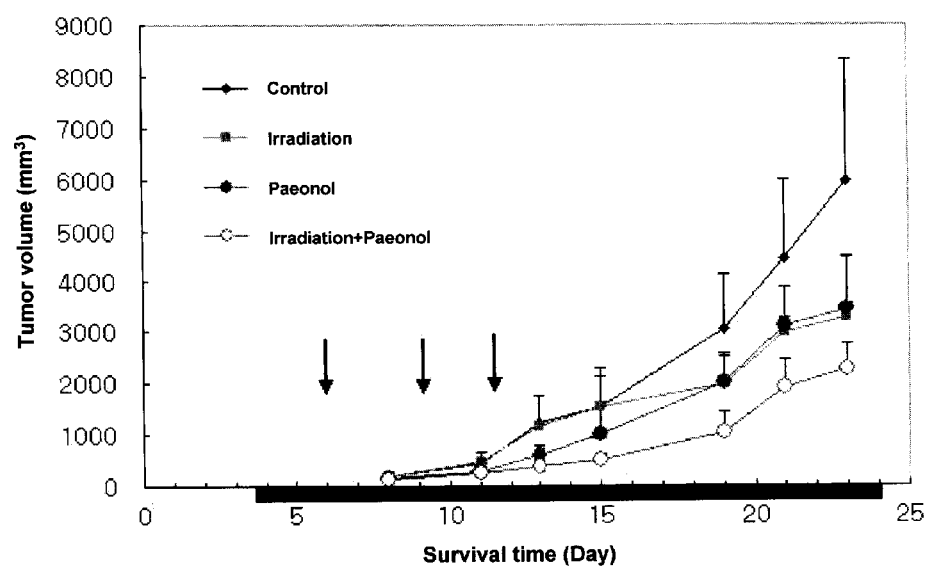

[Fig. 9]
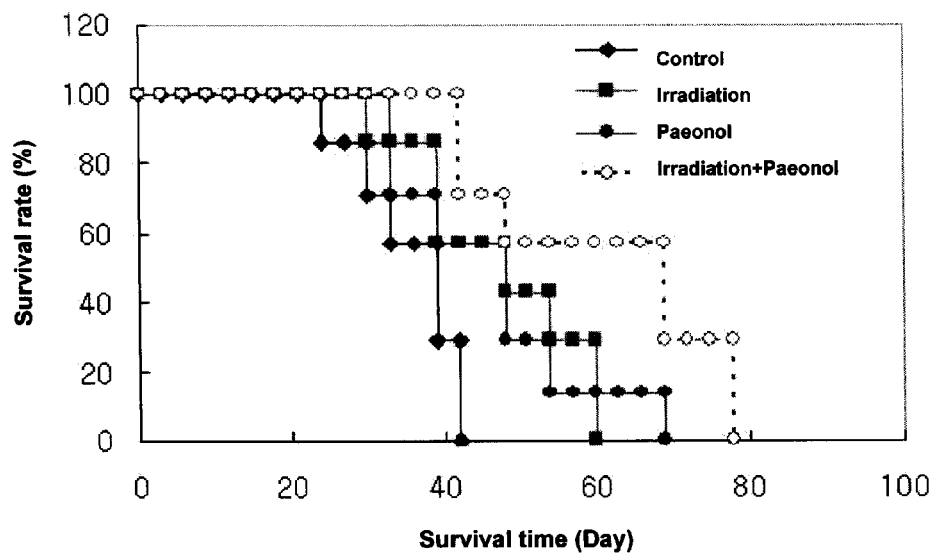
[Fig. 10]
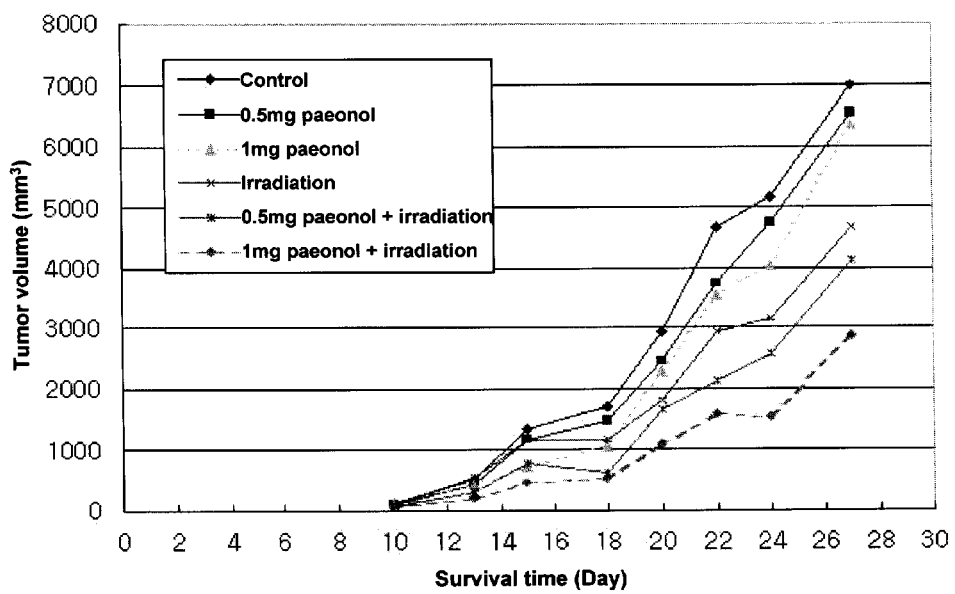

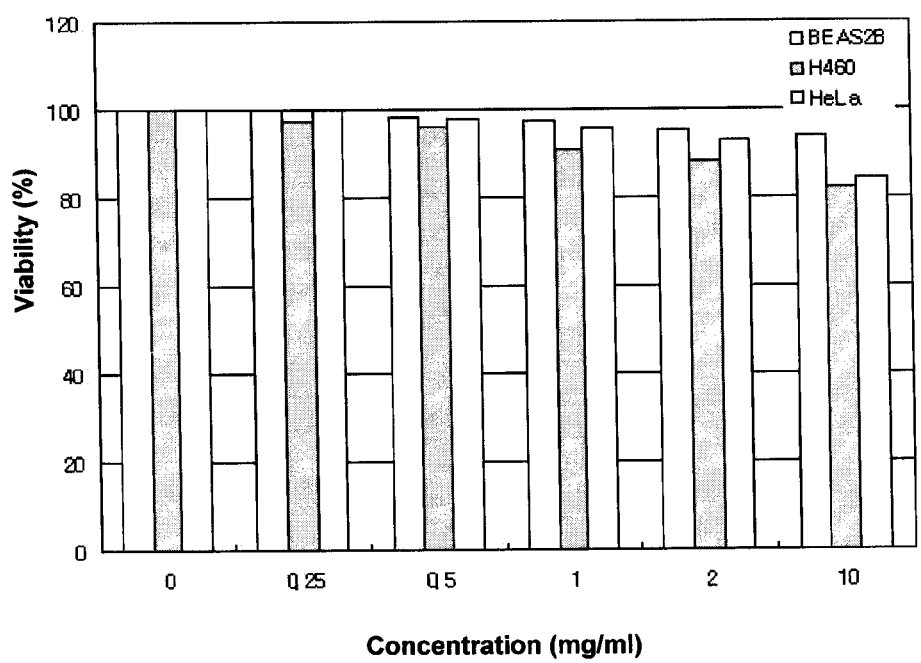
[Fig. 11]

USE OF PAEONOL FOR INHIBITING ANGIOGENESIS OR FOR ENHANCING RADIOSENSITIZATION

TECHNICAL FIELD

The present invention relates to a composition comprising paeonol of formula (I) or a pharmaceutically acceptable salt thereof as an active ingredient for inhibiting angiogenesis, or for enhancing radiosensitization.

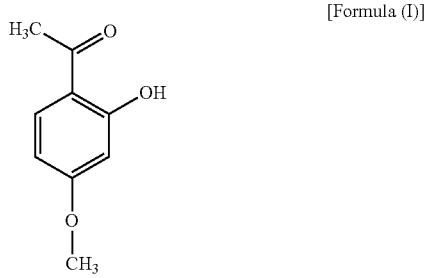

[Formula (I)]

The present invention also relates to novel use of paeonol of formula (I) or a pharmaceutically acceptable salt thereof for the manufacture of a composition for inhibiting angiogenesis, or for the manufacture of a composition for enhancing radiosensitization. Also, the present invention relates to a method for inhibiting angiogenesis which comprises administrating to a subject in need thereof an effective amount of paeonol of formula (I) or a pharmaceutically acceptable salt thereof, or a method for enhancing radiosensitization which comprises administrating an effective amount of paeonol of formula (I) or pharmaceutically acceptable salts thereof to a subject in need of radiotherapy.

BACKGROUND ART

The angiogenesis is the process of generating new capillary blood vessels from the existing ones.

Neovascularization is tightly regulated, and its activation occurs in embryogenic development, tissue remodeling, wound healing, and periodic cycles of corpus luteum development (Folkman and Cotran, *Int. Rev. Exp. Pathol.* 16, p 207-248, 1976).

In adults, the endothelial cells are growing very slowly as compared with other types of cells in the body. However, the proliferation of these cells is induced by pro-angiogenic cytokines, inflammation mediators and activated proteolytic enzymes.

Not only reorganization of the blood vessels by migration, proliferation, and differentiation of endothelial cells, but also degradation of the extracellular matrix is required for angiogenesis.

By the failure of regulation of angiogenesis, some pathological syndromes are developed. Pathological angiogenesis is involved in many diseases. For example, cardiovascular diseases such as angioma, anigofibroma, vascular deformity, atherosclerosis, synechia and edemic sclerosis; and ophthalmic diseases such as neovascularization after cornea implantation, neovascular glaucoma, diabetic retinopathy, angiogenic corneal disease, macular degeneration, pterygium, retinal degeneration, retrolental fibroplasias and granular conjunctivitis are related to angiogenesis. Chronic inflammatory diseases such as arthritis; dermatological disease such as psoriasis, telangiectasis, pyogenic granuloma, seborrhenic dermatitis and acne; growth and metastasis of cancer are also angiogenesis-dependent diseases (D'Amato R J and Adamis A P, *Ophthalomol.* 102, p 1261-1262, 1995; Arbiser J L, *J. Am. Acad. Derm.* 34(3), p 486-497, 1996; O'Brien K D et al. *Circulation* 93(4), p 672-682, 1996; Hanahan D and Folkman J, *Cell* 86, p 353-364, 1996).

Arthritis, a well-known inflammatory disease, is initiated as an autoimmune disease. As the progression of the inflammation, the growth of vascular endothelial cell in the synovial cavity is activated by the cytokines. The cartilage in the articulation is finally destroyed by the formation of articular lamina leak (Kocb A E, Polverini P J, and Lcibovich S J, *Arth. Rheum.* 29, p 471-479, 1986; Stupack D G, Storgard C M, and Cheresh D A, *Braz. J. Med. Biol. Res.* 32, p 578-581, 1999; Koch A E, *Arth. Rheum.* 41, p 951-962, 1998).

Many people are losing their eyesight all over the world because of various ocular diseases (Jeffrey M I and Takayuki A, *J. Clin. Invest.* 103, p 1231-1236, 1999). For example, macular degeneration, diabetic retinopathy, premature infant's retinopathy, retrolental fibroplasia, neovascular glaucoma, and angiogenic corneal disease are related to angiogenesis (Adamis A P, Aiello L P, and D'Amato R A, *Angiogenesis* 3, p 9-14, 1999). Diabetic retinopathy is one of diabetic complications, and many diabetic patients became blindness due to the infiltration of the capillary blood cells into the vitreous humor.

Psoriasis is caused by extremely active proliferation of skin cells. Fast growing cells require sufficient blood supply, and angiogenesis is abnormally induced in psoriasis (Folkman J, *J. Invest. Dermatol.* 59, p 40-48, 1972).

Angiogenesis is also closely related to atherosclerosis. It was reported that angiogenesis occurred in plaques of coronary artery so plaques became unstable to cause bleeding (Chen F, Eriksson P, Kimura T, Herzfeld I, and Valen G. *Coron. Artery Dis.* 16(3), p 191-197, 2005)

In case of obesity, adipose tissue can be regulated by capillary blood vessel structure so the treatment of anti-angiogenic inhibitors reduces body weight and adipose tissue in the dose-dependent manner (Rupnick M A et al. *Proc. Natl. Acad. Sci. U.S.A.* 99(16), p 10730-10735, 2002).

Recently, it was suggested that angiogenic factors were highly expressed in Alzheimer's disease patient' brain according to both blood flow reduction and inflammation so the increase of angiogenesis caused beta-amyloids to be deposited and neurotoxic peptides were secreted. Anti-angiogenic drug which targets on endothelial cells of abnormal brain can be used for the prevention and treatment of Alzheimer's disease (Vagnucci A H et al. *Lancet* 361, p 605-608, 2003).

As mentioned above, angiogenesis is closely related to initiation and progression of many diseases. Therefore, inhibitors of angiogenesis can be the good candidates for the treatment of those diseases. Many efforts have been made toward the development of angiogenesis inhibitors in order to prevent and/or treat those diseases.

It has been reported that angiogenesis is inhibited by horse chestnut extract (Korea Patent No. 533777), gluocosamine and its salts (Korea Patent No. 465229), *Ginkgo biloba* extract (Korea Patent No. 417172), ticlopidine (Korea Patent No. 455531), and *Melissa officinalis* extract (Korea Patent No. 500298).

Desirable angiogenesis inhibitors should not have toxic or adverse effect with good patient compliance because inhibitors need to be administered for a long time. Therefore, the development of angiogenesis inhibitors as pharmaceuticals and nutraceuticals without toxic effects is required.

Angiogenesis is essential to metastasis and growth of cancer. New blood vessels not only provide nutrients and oxygen to fast-growing cancer cells, but also give ways of entering to the blood stream resulting metastasis (Folkman and Tyler, Cancer Invasion and Metastasis, Biologic mechanisms and Therapy (S. B. Day ed.) Raven press, New York, p 94-103, 1977; Polverini P J, Critical Reviews in Oral Biology 6(3), p 230-247, 1995).

Currently, a large variety of chemotherapy and immunotherapy are applied in the treatment of cancer, but the efficacy of the therapies is limited and nothing can successfully extend the life of cancer patients due to the lack of anti-metastasis effects.

The methods for cancer treatment can be classified into surgery, radiotherapy, and chemotherapy and these therapies show about 50% of cure rate. About 35% among Korean cancer patients and about 50% among American cancer patients receive radiotherapy, and the role of radiotherapy is increased as the number of cancer patients receiving radiotherapy is increased.

Radiotherapy, which is essential method for the treatment of various cancers, has some problems such as radiation resistance of cancer cell and damage of normal tissue by high dose of radiation.

In order to enhance the efficacy of radiotherapy, many researches for the development of radiosensitizer have been conducted, and apoptosis inducer stimulating cellular signal transducers or cancer cell-specific receptor, cell cycle disrupter, and transcription factor inhibitor are considered as radiosensitizer.

It is known that combinational treatment of anti-cancer drug such as Taxol and 5-fluorouracil enhances the efficacy of radiotherapy. Tirapazamine, which isn't anti-cancer drug itself and is used in radiotherapy, has effects on only hypoxic tumor cell but weak effects on clinical radiotherapy because hypoxic intratumoral pressure prevents drug delivery into tumor.

However, when anti-cancer drugs are used in combination with radiotherapy, toxic effects of anti-cancer drugs can appear with adverse effects of radiotherapy such as inflammation, gastrointestinal disorder, nausea, vomiting, and diarrhea.

Therefore, the development of radiosensitizer, which has less adverse effects and solves the above problems, is required in order to treat various cancer diseases efficiently by radiotherapy.

Paeonol is one of active ingredients from *Paeonia suffruticosa* traditionally used in oriental medicine, and it is known to have antibiotic, anti-inflammatory, sedative, and immune-stimulating activities (Chou T C, *Br. J. Pharmacol.*, 139(6), p 1146-52, 2003; Kim S H et al., *Int. Immunopharmacol.*, 4(2), p 279-87, 2004). Paeonol is effect on stabilizing muscle and skin tissue, so it is used for anti-irritant and anti-inflammation on skin and mouth. Because paeonol has natural mint flavor, it is used as oral deodorant. Paeonol is also included in toothpaste in order to relieve toothache during tooth brushing, and it is also used for the relief of muscle pain, arthralgia, and neuralgia.

Unexpectedly, the inventors have found that paeonol has radiosensitization-enhancing activity as well as anti-angiogenic activity, and then completed the present invention.

DISCLOSURE

Technical Solution

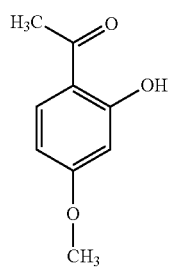

[Formula (I)]

It is an object of the present invention to provide a composition for inhibiting angiogenesis comprising paeonol of formula (I) or a pharmaceutically acceptable salt thereof as an active ingredient.

It is another object of the present invention to provide a composition for enhancing radiosensitization comprising paeonol of formula (I) or a pharmaceutically acceptable salt thereof as an active ingredient.

It is still another object of the present invention to provide a novel use of paeonol of formula (I) or a pharmaceutically acceptable salt thereof for the manufacture of a composition for inhibiting angiogenesis.

It is yet another object of the present invention to provide a novel use of paeonol of formula (I) or a pharmaceutically acceptable salt thereof for the manufacture of a composition for enhancing radiosensitization.

It is still another object of the present invention to provide a method for inhibiting angiogenesis which comprises administrating to a subject in need thereof an effective amount of paeonol of formula (I) or a pharmaceutically acceptable salt thereof.

It is yet another object of the present invention to provide a method for enhancing radiosensitization which comprises administrating an effective amount of paeonol of formula (I) or pharmaceutically acceptable salts thereof to a subject in need of radiotherapy.

The present invention will be described more specifically as below.

Unless indicated differently, the terms used in the present invention will be regarded to be used as same meaning over the present specification.

The present invention provides a composition for inhibiting angiogenesis comprising paeonol of formula (I) or a pharmaceutically acceptable salt thereof as an active ingredient.

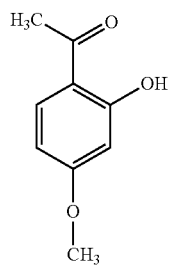

[Formula (I)]

In an embodiment of the present invention, the composition is for the prevention, improvement or treatment of angiogenesis-related diseases.

In another embodiment of the present invention, the angiogenesis-related disease is selected from the group consisting of cancer, angioma, angiofibroma, diabetic retinopathy, premature infant's retinopathy, neovascular glaucoma, corneal disease induced by angiogenesis, involution macula, macular degeneration, pterygium, retinal degeneration, retrolental fibroplasias, granular conjunctivitis, psoriasis, telangiectasis, pyogenic granuloma, seborrheic dermatitis, acne, arthritis, atherosclerosis, obesity and Alzheimer's disease.

In another embodiment of the present invention, the composition is a pharmaceutical composition.

In another embodiment of the present invention, the composition is a nutraceutical composition.

Also, the present invention provides a composition for enhancing radiosensitization comprising paeonol of formula (I) or a pharmaceutically acceptable salt thereof as an active ingredient.

In an embodiment of the present invention, the composition comprises 1-99 w/w % of paeonol or pharmaceutically acceptable salts thereof.

In another embodiment of the present invention, the composition is a pharmaceutical composition.

In another embodiment of the present invention, the composition is a nutraceutical composition.

The term "composition" as used hereinbefore or hereinafter is regarded as including any product formed by combination of specific ingredients directly or indirectly as well as a product containing the specific ingredients.

The active ingredient of the present invention, "paeonol" is a compound of formula (I) as below.

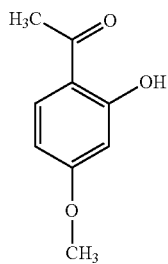

[Formula (I)]

Paeonol can be obtained by extraction, isolation, and purification from the root of *Paeonia suffruticosa, Paeonia moutan,* or *Paeonia lactiflora* in accordance with a conventional method, or by synthesis according to Bensari & Zaveri method (Bensari A and Zaveri N T, *Synthesis* 2, p 267-271, 2003), and it is also possible to use commercially available paeonol.

For example, paeonol of the present invention can be obtained by the following procedure:

1) 3 to 20 volumes of water, C1-C4 lower alcohol, or their mixture is added to 1 kg of dried root powder of *Paeonia suffruticosa, Paeonia moutan,* or *Paeonia lactiflora*. The mixture is allowed to extract at a temperature ranging from room temperature to 100° C., for a period ranging from 6 hours to 10 days by conventional extraction methods such as hot water extraction, cold extraction, reflux cold extraction, and extraction with ultrasound. The extraction process may be repeated 2 to 5 times.

2) The crude extract is obtained by infiltration, rotary decompression concentration, or freezing drying.

3) The crude extract is dissolved in water, and then the suspension is fractionated with organic solvent such as hexane, chloroform, methylenechloride, ethylacetate, and n-butamol.

4) The obtained fraction is applied to silica gel chromatography with hexane:acetone solvent ranging from 60:1 to 1:1. 5) Paeonol can be obtained by recrystalization of fractions obtained in step 4.

Paeonol of the present invention can be used on the pharmaceutical purpose in the form of paeonol itself or pharmaceutically acceptable salts thereof. Examples of suitable salts include, but are not limited to, chloride, sulfate, nitrate, phosphate, fluorate, bromate, formate, acetate, tartarate, lactate, citrate, fumarate, malate, succinate, methanesulfonate, benzenesulfonate, toluenesulfonate, and naphthalenesulfonate.

The composition of the present invention comprising paeonol shows lower contents of hemoglobin in paeonol-treated groups compared with control group in mouse Matrigel assay.

The composition of the present invention comprising paeonol has superior activities on the prevention and treatment for cancer, thus elongates the lifetime of tumor-induced organisms.

Also, the composition of the present invention comprising paeonol can be effectively used for the prevention and treatment for cancer, because it enhances the inhibition of tumor growth and the survival time of tumor-induced organisms in combination with the administration of anti-cancer drug.

Moreover, the composition of the present invention can enhance anti-cancer effects of cancer therapy by itself or in combination with radiotherapy.

The composition of the present invention comprising paeonol reduces the clone formation of cancer cell lines (HeLa, LLC, NCI-H460) in combination with radiotherapy. The combinational treatment of paeonol and radiotherapy enhances the sensitivity of cancer cell against radiation, decreases the viability of cancer cell, inhibits the growth of tumor, elongates the survival time of tumor-induced organisms, and enhances the survival rates of tumor-induced organisms.

Therefore, the composition of the present invention comprising paeonol has superior effects on enhancing radiosensitization of various cancers (lung carcinoma, uterine carcinoma, melanoma, etc.) in combination with radiotherapy, so that the combination treatment of paeonol and radiotherapy reduces therapeutic radiation dose and adverse effects of radiotherapy such as the damage of normal cell.

Also, the composition of the present invention comprising paeonol does not the cytotoxicity on normal and cancer cell, and has neither acute toxicity nor adverse effects on treated animals during oral administration thereof.

The composition of the present invention can be a pharmaceutical composition or a nutraceutical composition according to the purpose of the composition.

The composition of the present invention can comprise not only paeonol but also other ingredients having anti-angiogenic activity, and can additively comprise other active ingredients if necessary.

The composition of the present invention may further comprise one or more pharmaceutically or physiologically acceptable carriers to be formulated appropriately for administration. The pharmaceutically or physiologically acceptable carriers can be, for example, saline, autoclaved water, Ringer's solution, buffered saline, dextrose, maltodextrin, glycerol, ethanol, and the mixture thereof. If necessary, the composition of the present invention can comprise conventional additives such as antioxidant, buffer and antiseptic substances. The composition of the present invention can also comprise pharmaceutically and physiologically acceptable additives such as diluent, dispersing agent, surfactant, solvent, disintegrating agent, sweetener, binder, coating agent, blowing agent, lubricant, glidant, or flavoring agent. By using conventional methods or the written text of Remington's Pharmaceutical Science (Mack Publishing Company, Easton Pa.), the composition of the present composition can be formulated in any desirable forms according to disease or ingredient.

The pharmaceutical composition of the present invention can be formulated in any form such as granule, powder, tablet, coated tablet, capsule, pill, syrup, drop, injectable preparation (solution, suspension, and emulsion), or sustained release formulation of an active ingredient.

The pharmaceutical composition of the present invention can be administered via various routes including intravenous, intra-arterial, intraperitoneal, intrathoracic, transdermal, nasal, inhalation, topical, rectal, oral, ocular, and subcutaneous introduction, according to conventional method of administration.

The pharmaceutical composition can comprise 1-99 w/w % of paeonol or pharmaceutically acceptable salts thereof. For the pharmaceutical composition, desirable dosage of paeonol or pharmaceutically acceptable salts thereof can be 0.1 mg/kg~500 mg/kg per day for adult, and can be determined by various factors such as the sort and severity of patient's symptom, the content of active ingredient, the content and sort of other ingredients, the type of formulation, patient's parameters (age, body weight, health status, sex), food, dosing time, administration route, the ratio of composition, time of treatment, and other co-administrated drug.

The nutraceutical composition of the present invention can take any form of foods. For example, it can be dried with carriers and then be produced as capsule, or processed to tablet, granule, powder, beverage, gruel, etc, according to the conventional methods in the art.

The nutraceutical composition can comprise 1-99 w/w % of paeonol or pharmaceutically acceptable salts thereof. For the nutraceutical composition, desirable intake of paeonol or acceptable salts thereof can be 0.1 mg/kg~500 mg/kg per day for adult.

Also, the present invention provides a novel use of paeonol of formula (I) or a pharmaceutically acceptable salt thereof for the manufacture of a composition for inhibiting angiogenesis.

In an embodiment of the present invention, the composition is used for the prevention, improvement or treatment of angiogenesis-related diseases.

In another embodiment of the present invention, the angiogenesis-related disease is selected from the group consisting of, angioma, angiofibroma, diabetic retinopathy, premature infant's retinopathy, neovascular glaucoma, corneal disease induced by angiogenesis, involution macula, macular degeneration, pterygium, retinal degeneration, retrolental fibroplasias, granular conjunctivitis, psoriasis, telangiectasis, pyogenic granuloma, seborrheic dermatitis, acne, arthritis, atherosclerosis, obesity and Alzheimer's disease.

In another embodiment of the present invention, the composition is a pharmaceutical composition.

In another embodiment of the present invention, the composition is a nutraceutical composition.

Furthermore, the present invention provides a novel use of paeonol of formula (I) or a pharmaceutically acceptable salt thereof for the manufacture of a composition for enhancing radiosensitization.

In an embodiment of the present invention, the composition comprises 1-99 w/w % of paeonol or pharmaceutically acceptable salts thereof.

In another embodiment of the present invention, the composition is a pharmaceutical composition.

In another embodiment of the present invention, the composition is a nutraceutical composition.

Also, the present invention provides a method for inhibiting angiogenesis which comprises administrating to a subject in need thereof an effective amount of paeonol of formula (I) or a pharmaceutically acceptable salt thereof.

In an embodiment of the present invention, the method is for the prevention, improvement or treatment of angiogenesis-related diseases.

In another embodiment of the present invention, the angiogenesis-related disease is selected from the group consisting of cancer, angioma, angiofibroma, diabetic retinopathy, premature infant's retinopathy, neovascular glaucoma, corneal disease induced by angiogenesis, involution macula, macular degeneration, pterygium, retinal degeneration, retrolental fibroplasias, granular conjunctivitis, psoriasis, telangiectasis, pyogenic granuloma, seborrheic dermatitis, acne, arthritis, atherosclerosis, obesity and Alzheimer's disease.

In another embodiment of the present invention, the paeonol of formula (I) or a pharmaceutically acceptable salt thereof is comprised in a pharmaceutical composition.

In another embodiment of the present invention, the paeonol of formula (I) or a pharmaceutically acceptable salt thereof is comprised in a nutraceutical composition.

Furthermore, the present invention provide a method for enhancing radiosensitization which comprises administrating an effective amount of paeonol of formula (I) or pharmaceutically acceptable salts thereof to a subject in need of radiotherapy.

In an embodiment of the present invention, the paeonol of formula (I) or a pharmaceutically acceptable salt thereof is comprised a composition to be administrated, in amount of 1-99 w/w % of the composition.

In another embodiment of the present invention, the paeonol of formula (I) or a pharmaceutically acceptable salt thereof is comprised in a pharmaceutical composition.

In another embodiment of the present invention, the paeonol of formula (I) or a pharmaceutically acceptable salt thereof is comprised in a nutraceutical composition.

The method of the present invention can be performed by using paeonol of formula (I) or a pharmaceutically acceptable salt thereof, or the above-described composition comprising paeonol of formula (I) or a pharmaceutically acceptable salt thereof.

The paeonol of formula (I) or a pharmaceutically acceptable salt thereof, or the composition of the present invention can be administered via various routes including intravenous, intra-arterial, intraperitoneal, intrathoracic, transdermal, nasal, inhalation, topical, rectal, oral, ocular, and subcutaneous introduction, according to conventional method of administration.

Desirable dosage of the paeonol of formula (I) or a pharmaceutically acceptable salt thereof for inhibiting angiogenesis or for enhancing radiosensitization can be 0.1 mg/kg~500 mg/kg per day for adult, and can be determined by various factors such as the sort and severity of patient's symptom, the content of active ingredient, the content and sort of other ingredients, the type of formulation, patient's parameters (age, body weight, health status, sex), food, dosing time, administration route, the ratio of composition, time of treatment, and other co-administrated drug.

For enhancing radiosensitization, the paeonol of formula (I) or a pharmaceutically acceptable salt thereof can be administrated to a subject in need of radiotherapy before and/or during radiotherapy.

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

DESCRIPTION OF DRAWINGS

FIG. 1 is a graph showing inhibitory effect of paeonol on angiogenesis in mouse Matrigel model.

FIG. 2 is a graph showing inhibitory effect of paeonol on tumor growth in solid tumor induced mouse.

FIG. 3 is a graph showing effect of paeonol on elongation of survival time in solid tumor induced mouse.

FIG. 4 is a graph showing synergy effect of paeonol on inhibition of tumor growth in combination with other anticancer drugs.

FIG. 5 is a graph showing synergy effect of paeonol on elongation of survival time in combination with other anticancer drug.

FIG. 6 is a graph showing effect of paeonol on radiosensitization of human lung cancer cell.

FIG. 7 is a graph showing effect of paeonol on radiosensitization of human uterine carcinoma cell.

FIG. 8 is a graph showing decrease of tumor volume in lung cancer cell-injected mouse by treatment of radiation and paeonol.

FIG. 9 is a graph showing increase of survival rates in lung cancer cell-injected mouse by treatment of radiation and paeonol.

FIG. 10 is a graph showing decrease of tumor volume in melanoma cell-injected mouse by treatment of radiation and paeonol.

FIG. 11 is a graph showing survival rates of normal and cancer cell by the treatment of paeonol.

MODE FOR INVENTION

To investigate effects of the present composition comprising paeonol on angiogenesis or radiosensitization, paeonol was purified from the root of *Paeonia suffruticosa* and then activities of paeonol were investigated using animal experiment.

Purification and Identification of Paeonol 2 kg of dried root powder of *Paeonia suffruticosa* was extracted in 5 liters of methanol at 70° C. for 5 hours by reflux extraction, and the extraction was repeated three times. The filtrated extract was lyophilized, and then 500 g of methanol extract was obtained. Methanol extract was suspended in 3 liters of water, and then was fractionated with 3 liters of hexane three times. Hexane-soluble fraction was lyophilized, and then 67 g of hexane fraction was obtained. Hexane fraction was applied into silica gel column chromatography using hexane:acetone solvent (60:1 to 1:1), and then 7 fractions (Fr. 1~7) were obtained.

TLC(Thin Layer Chromatography) Data
Silica gel plate 60 F254 (Merck)
hexane:aceotone=3:1
Rf value: 0.44 (detection at UV 254 nm)

Precipitant obtained from Fr. 2 was recrystalized with ethanol, and then compound 1 (2100 mg) showing needle-shaped white crystal was obtained.

Compound 1 (Paeonol)

mp 48~50° C., IR (KBr) $v_{max}$ cm$^{-1}$: 3400, 2940, 1725, 1625, 1570, 1500; $^1$H-NMR (400 MHz, CDCl$_3$) δ: 2.55 (3H, s, CH$_3$), 3.83 (3H, s, OCH$_3$), 6.40~6.50 (2H, m, H-3, H-5), 7.60 (1H, d, J=10.0 Hz, H-6), 12.60 (1H, s, OH); $^{13}$C-NMR (100 MHz, CDCl$_3$) δ: 114.1 (C-1), 165.2 (C-2), 100.8 (C-3), 166.1 (C-4), 107.6 (C-5), 132.6 (C-6), 202.5 (C=O), 55.4 (OCH$_3$), 26.1 (CH$_3$).

Because the above data of compound 1 was coincided with the data of paeonol written in the literature (Kwon et al., *Kor. J. Pharmacogn.* 30, p 340-344, 1999), compound 1 was identified as paeonol.

Example 1

Inhibitory Effects of Paeonol on Angiogenesis Using Animal Experiment (Mouse Matrigel Model)

Effects of oral administration of paeonol on angiogenesis were quantitatively investigated in mouse Matrigel model.

The mixture of 0.4 ml of Matrigel, 50 ng/ml of basic fibroblast growth factor (bFGF) and 40 units/ml of heparin which are angiogenesis-inducing factor was subcutaneously injected into C57BL/6 female mice (SLC Co., Japan; 6 week-old) adapted for 1 week.

0.5 mg of the above isolated paeonol was dissolved in 0.2 ml of 20% ethanol, and then 0.5 mg per mouse of paeonol (1 mg/day) was orally administrated into the treated group (n=8) twice a day for 4 days. In the other hand, 0.2 ml of 20% ethanol was also orally administrated into the control group (n=8) in the same manner as treated group.

On the fifth day of oral administration, Matrigel was separated from excised skin of each mouse, and the level of hemoglobin in the Matrigel was measured in order to determine the inhibition of angiogenesis quantitatively.

As shown in FIG. 1, the hemoglobin content of treated group was reduced up to 33% as compared with that of control group, and angiogenesis was inhibited by about 67%. Therefore, it was confirmed that the composition of the present invention comprising paeonol has anti-angiogenic activity.

Example 2

Inhibitory Effect of Paeonol on the Growth of Solid Tumor

Effects of administering the present composition comprising paeonol on the growth of solid tumor were investigated.

For the induction of primary tumor, B16BL6 melanoma cells (1×10$^6$) suspended in 0.2 ml of PBS (potassium-buffered saline) were subcutaneously injected into C57BL6 female mice (SLC Co., Japan; 6 week-old, 20-25 g of body weight) adapted for 1 week.

0.5 mg of the above isolated paeonol was dissolved in 0.2 ml of 20% ethanol, and then 0.5 mg per mouse of paeonol (1 mg/day) was orally administrated into the treated group (n=7) twice a day for 17 days after injecting cancer cells. In the other hand, 0.2 ml of 20% ethanol was also orally administrated into the control group (n=7) in the same manner as treated group.

The size of tumor was measured once per 1-2 days for 17 days after injecting cancer cells and then the volume of tumor was calculated in accordance with the following equation, (width)$^2$×(length)×0.52.

As shown in FIG. 2, oral administration of paeonol with the dosage of 1 mg per day for 17 days prevented tumor size compared with the control group, and inhibited tumor growth by 48%.

Therefore, it was confirmed that the composition of the present invention comprising paeonol has inhibitory effects on tumor growth.

Example 3

Lifetime Elongation of Tumor-Induced Mice by Administration of Paeonol

Effects of the present composition comprising paeonol on lifetime elongation of tumor-induced mice were investigated.

For the induction of primary tumor, B16BL6 melanoma cells (1×10$^6$) suspended in 0.2 ml of PBS were subcutaneously injected into C57BL6 female mice (SLC Co., Japan; 6 week-old, 20-25 g of body weight) adapted for 1 week.

0.5 mg of the above isolated paeonol was dissolved in 0.2 ml of 20% ethanol, and then 0.5 mg per mouse of paeonol (1 mg/day) was orally administrated into the treated group (n=7) twice a day for 22 days after injecting cancer cells. In the other hand, 0.2 ml of 20% ethanol was also orally administrated into the control group (n=7) in the same manner as treated group.

As shown in FIG. 3, the number of dead mice was increased in proportion to the incubation time. After 22 days, one of control group survived whereas three of treated group survived. The survival rates of treated and control groups were 43% and 14%, respectively. Therefore, it was confirmed that the composition of the present invention comprising paeonol has enhancing effects on lifetime and survival rate of solid tumor-induced mice.

Example 4

Inhibitory Effects of Paeonol on Tumor Metastasis

Inhibitory effects of the present composition comprising paeonol on tumor metastasis in tumor-induced mice were investigated.

In order to induce tumor, B16BL6 melanoma cells (5×10$^4$) suspended in 0.2 ml of PBS were intravenously injected into tails of C57BL6 female mice (SLC Co., Japan; 6 week-old) adapted for 1 week.

0.25 mg of the above isolated paeonol was dissolved in 0.2 ml of 20% ethanol, and then 0.25 mg per mouse of paeonol (0.5 mg/day) was orally administrated into the treated group (n=6) twice a day for 14 days after injecting cancer cells. In the other hand, 0.2 ml of 20% ethanol was also orally administrated into the control group (n=6) in the same manner as treated group. After 14 days, mice were dissected, and then the numbers of colonies, which metastasized into lung, were counted.

Control group had 213±60 colonies per mouse whereas treated group had 132±80 colonies. Oral administration of paeonol inhibited metastasis into lung by 38%. Therefore, it was confirmed that the composition of the present invention comprising paeonol has inhibitory effects on tumor metastasis.

Example 5

Synergy Effect of Paeonol in Combination with Other Anti-Cancer Drug 5-1) Inhibitory Effect on Tumor Growth Synergy effect of paeonol in combination with anti-cancer drug, 5-fluorouracil (5-FU) was investigated.

For the induction of primary tumor, B16BL6 melanoma cells (1×10$^6$) suspended in 0.2 ml of PBS were subcutaneously injected into C57BL6 female mice (SLC Co., Japan; 6 week-old, 20-25 g of body weight) adapted for 1 week.

In 5-FU & paeonol treated group (n=7), 70 mg/kg per mouse of 5-FU was intraperitoneally injected at 3 day and 6 day after injecting cancer cells, and 1 mg per mouse of paeonol dissolved in 0.2 ml of 20% ethanol was orally administrated twice a day for 21 days after injecting cancer cells. In 5-FU treated group (n=7), 70 mg/kg per mouse of 5-FU was treated in the same manner as 5-FU & paeonol treated group. In the other hand, 0.2 ml of 20% ethanol was also orally administrated into control group (n=7) and 5-FU treated group in the same manner as 5-FU & paeonol treated group. The size of tumor was measured once per 1-2 days for 21 days after injecting cancer cells and then the volume of tumor was calculated in accordance with the following equation, (width)$^2$×(length)×0.52.

As shown in FIG. 4, tumor growths of 5-FU treated group and 5-FU & paeonol treated group were inhibited by 50% and 69% compared with that of control group, respectively. It was confirmed that the combinational treatment with anti-cancer drug and anti-angiogenic paeonol has more inhibitory effect on tumor growth than the treatment of anti-cancer drug itself.

5-2) Lifetime Elongation of Tumor-Induced Mice

Effects of paeonol on lifetime elongation of tumor-induced mice were investigated.

For the induction of primary tumor, B16BL6 melanoma cells (1×10$^6$) suspended in 0.2 ml of PBS were subcutaneously injected into C57BL6 female mice (SLC Co., Japan; 6 week-old, 20-25 g of body weight) adapted for 1 week.

In 5-FU & paeonol treated group, 70 mg/kg per mouse of 5-FU was intraperitoneally injected at 3 day and 6 day after injecting cancer cells, and 1 mg per mouse of paeonol dissolved in 0.2 ml of 20% ethanol was orally administrated twice a day for 21 days after injecting cancer cells. In 5-FU treated group, 70 mg/kg per mouse of 5-FU was treated in the same manner as 5-FU & paeonol treated group. In the other hand, 0.2 ml of 20% ethanol was also orally administrated into control group and 5-FU treated group in the same manner as 5-FU & paeonol treated group.

As shown in FIG. 5, the number of dead mice was increased in proportion to the incubation time. After 22 days, each one of control group (n=7) and 5-FU treated group (n=7) survived (survival rate 14%) whereas four of 5-FU & paeonol treated group (n=7) survived (survival rate 57%). Therefore, it was confirmed that the combinational treatment with anti-cancer drug and anti-angiogenic paeonol has more enhancing effects on lifetime and survival rate of solid tumor-induced than the treatment of anti-cancer drug itself.

Example 6

Effect of Paeonol on Radiosensitization in Lung Carcinoma Cell Line, H460

Effect of treatment of paeonol during radiation into lung carcinoma cell line on radiosensitization was investigated.

$10^2$-$10^3$ of human lung carcinoma cell line H460 was irradiated with various doses of radiation (0, 1, 2, 3 Gy) for control groups (n=3) just once, and was irradiated with 3 Gy of radiation and the above isolated paeonol (1 μg/ml, 2 μg/ml in 20% ethanol) for paeonol treated group (n=3) just once. At 7 day after irradiation, the clone formation (%) of each groups were measured and then the survival rates of each groups were compared with each other.

Irradiation with high dose of radiation into cancer cell line prevents clone formation.

As shown in Table 1 and FIG. 6, irradiation with 0, 1, 2 and 3 Gy of radiation showed 100%, 77.0%, 49.3% and 30.7% of clone formation, respectively.

In the case of radiation & paeonol treated groups, treatment with 1 μg/ml and 2 μg/ml of paeonol showed 25.8% and 21.2% of clone formation, respectively.

The clone formation of radiation & paeonol treated groups decreased by 16% (1 μg/ml of paeonol) or 31% (2 μg/ml of paeonol) compared with that of control group irradiated with 3 Gy of radiation.

Therefore, it was confirmed that treatment of paeonol into lung carcinoma cell line during irradiation enhances the radiosensitization of lung carcinoma cell line.

TABLE 1

| Radiation (Gy) | Paeonol (μg/ml) | Clone formation (%) |
|---|---|---|
| 0 | — | 100 |
|  | 1 | 100 |
|  | 2 | 100 |
| 1 | — | 77 |
|  | 12 | 72.5 |
|  | 2 | 71.1 |
| 2 | — | 49.3 |
|  | 1 | 46.4 |
|  | 2 | 43.3 |
| 3 | — | 30.7 |
|  | 1 | 25.8 |
|  | 2 | 21.2 |

Example 7

Effect of Paeonol on Radiosensitization in Uterine Carcinoma Cell Line, HeLa Effect of treatment of paeonol during radiation into uterine carcinoma cell line on radiosensitization was investigated.

$10^2$-$10^3$ of human lung carcinoma cell line HeLa was irradiated with various doses of radiation (0, 1, 2, 3 Gy) for control groups (n=3) just once, and was irradiated with 3 Gy of radiation and the above isolated paeonol (1 μg/ml, 2 μg/ml in 20% ethanol) for paeonol treated group (n=3) just once. At 7 day after irradiation, the clone formation (%) of each groups were measured and then the survival rates of each groups were compared with each other.

As shown in Table 2 and FIG. 7, irradiation with 0, 1, 2 and 3 Gy of radiation showed 100%, 73.8%, 49.4%, and 15.9% of clone formation, respectively.

In the case of radiation & paeonol treated groups, treatment with 1 μg/ml and 2 μg/ml of paeonol showed 12.3% and 10.9% of clone formation, respectively.

The clone formation of radiation & paeonol treated groups decreased by 23% (1 μg/ml of paeonol) or 39% (2 μg/ml of paeonol) compared with that of control group irradiated with 3 Gy of radiation.

Therefore, it was confirmed that treatment of paeonol into uterine carcinoma cell line during irradiation enhances the radiosensitization of uterine carcinoma cell line.

TABLE 2

| Radiation (Gy) | Paeonol (μg/ml) | Clone formation (%) |
|---|---|---|
| 0 | — | 100 |
|  | 1 | 100 |
|  | 2 | 100 |
| 1 | — | 73.8 |
|  | 1 | 73.4 |
|  | 2 | 72.8 |
| 2 | — | 49.4 |
|  | 1 | 45.5 |
|  | 2 | 44.7 |
| 3 | — | 15.9 |
|  | 1 | 12.3 |
|  | 2 | 10.9 |

In accordance with the results of Table 1 and Table 2, it was confirmed that the treatment of paeonol into lung carcinoma cell line as well as uterine carcinoma cell line during irradiation enhances the radiosensitization of carcinoma cell lines, so it has enhancing effects on radiotherapy.

Example 8

Effect of Paeonol on Radiosensitization in Lung Carcinoma Cell Line, LLC-Transplanted Animal Effect of treatment of paeonol during radiation into lung carcinoma cell line-transplanted animal on radiosensitization was investigated.

$1 \times 10^6$ of mouse lung carcinoma cell line, LLC (Lewis lung carcinoma) cell were suspended in 0.2 ml of PBS, and then were injected into left leg of mouse in order to induce the tumor. LLC-transplanted mice were classified into 4 groups such as control group (n=10), irradiation-treated group (n=10), paeonol-treated group (n=10), and irradiation & paeonol-treated group (n=10).

After the volumes of tumor were about 100-200 mm$^3$ (6-7 day after LLC injection), 5 Gy of $^{60}$Co radiation was irradiated to irradiation-treated group and irradiation & paeonol-treated group three times at an interval of 2 or 3 days.

After the existence of tumor was detected by touching with hand (4 day after LLC injection), 5 mg/kg of paeonol dissolved in 20% ethanol was orally administered into paeonol-treated group and irradiation & paeonol group once a day for 20 days. For control group and irradiation group, 20% ethanol was orally administered in the same manner as paeonol-treated group.

Enhancing effects of paeonol in combination with radiation on efficacy of radiotherapy was determined by comparing both tumor growth rates and mouse survival rates of 4 groups with each other groups.

The sizes (width, length) of tumor were measured for 30 days at an interval of 2 or 3 days, and then the volumes of tumor were calculated by the following equation, (width)$^2$×

(length)×0.52. The tumor growth rates were also calculated by converting into the time which it takes for tumor volume to be 2000 mm³.

As shown in Table 3 and FIG. 8, it took 16 days for tumor volume to be 2000 mm³ for control group, whereas the tumor growth rates of irradiation-treated group, paeonol-treated group, and irradiation & paeonol-treated group were 19, 19, and 22 days, respectively. The tumor growth rates of irradiation-treated group and paeonol-treated group went down 1.2-fold as compared with that of control group whereas that of irradiation & paeonol-treated group went down 1.4-fold.

TABLE 3

| Group | Tumor growth rate (Time which it takes for tumor volume to be 2000 mm³) |
|---|---|
| LLC-injected group (control group) | 16 |
| LLC-injected, irradiation-treated group | 19 |
| LLC-injected, paeonol-treated group | 19 |
| LLC-injected, irradiation & paeonol-treated group | 22 |

As shown in FIG. 9, mice of irradiation & paeonol-treated group survived for 78 days whereas mice of control group, irradiation-treated group, and paeonol-treated group survived for 42, 60, and 69 days, respectively. The survival rate of irradiation & paeonol-treated group increased about 2 times compared with that of control group.

In accordance with the results of tumor-transplanted animal experiment, tumor growths of irradiation-treated group and paeonol-treated group were inhibited more than that of control group, and especially the combinational treatment of irradiation and paeonol inhibited tumor growth rate and increased the survival time and survival rate by enhancing radiosensitization with paeonol.

Therefore, it was confirmed that treatment of paeonol enhances the therapeutic efficacy of radiotherapy by increasing the radiosensitization.

Example 9

Effect of Paeonol on Radiosensitization in Melanoma-Transplanted Animal

Effect of treatment of paeonol during radiation into melanoma-transplanted animal on radiosensitization was investigated.

In order to induce primary tumor, B16BL6 melanoma cells (1×10⁶) suspended in 0.2 ml of PBS was subcutaneously injected into C57BL6 female mice (SLC Co., Japan; 6 week-old of body weight) adapted for 1 week.

Melanoma-transplanted mice were classified into 6 groups: control group (n=10), irradiation group (n=10), paeonol-treated groups (0.5 or 1 mg/kg per day) (n=10), and irradiation & paeonol-treated groups (0.5 or 1 mg/kg per day) (n=10), and then it was observed whether the combinational treatment of irradiation and paeonol enhances the radiosensitization of melanoma-transplanted animal.

5 Gy of ⁶⁰Co radiation was irradiated to irradiation-treated group and irradiation & paeonol-treated at 4 and 6 day after tumor injection. 0.5 mg/kg or 1.0 mg/kg of paeonol dissolved in 20% ethanol was orally administered once a day after tumor injection.

For control group and irradiation group, 20% ethanol was orally administered in the same manner as paeonol-treated group.

The sizes (width, length) of tumor were measured for 30 days at an interval of 2 or 3 days, and then the volumes of tumor were calculated by the following equation, (width)²×(length)×0.52.

During the experiment, any side effects and special features of tested animal were not found except for tumor.

As shown in FIG. 10, tumor volumes of paeonol-treated groups (0.5 mg/kg or 1.0 mg/kg of paeonol) and irradiation-treated group decreased by 6.4% (0.5 mg/kg of paeonol), 9.3% (1.0 mg/kg of paeonol, and 33.1% compared with that of control group, respectively. Irradiation & paeonol-treated groups decreased by 58.9% of the maximum, so it was confirmed that the combinational treatment of irradiation and paeonol is more effective on inhibition of tumor growth by enhancing the radiosensitization of tumor.

In the case of irradiation & paeonol-treated group (1.0 mg/kg of paeonol), tumor growth was more inhibited compared as irradiation & paeonol-treated group (0.5 mg/kg of paeonol), and it means that paeonol has concentration-dependent inhibitory effects on tumor growth.

Therefore, it was confirmed that treatment of paeonol enhances the therapeutic efficacy of radiotherapy by increasing the radiosensitization Example 10

Toxicity of Paeonol on Cell and Animal 10-1) Cytotoxicity Test on Cell

In order to examine the cytotoxicity of paeonol, 2×10⁵ of normal human lung cell (BEAS-2B), human lung carcinoma cell (NCI-H460), human uterine carcinoma cell (HeLa) were treated with various concentrations (0.25, 0.5, 1, 2, 10 μg/ml) of paeonol for 24 hours, and then viabilities of each cells were measured by MTT assay.

As shown in FIG. 11, all viabilities were decreased by paeonol in the concentration-dependent manner, and normal cell, NCI-H460, and HeLa showed 6%, 18%, and 15% of cytotoxicity in the treatment of 10 μg/ml of paeonol, respectively. Also, paeonol did not show enough toxicity to calculate $LD_{50}$ for both normal cell and cancer cell.

Therefore, it was confirmed that paeonol has hardly cytotoxicity against normal cell and show a little cytotoxicity against cancer cell.

10-2) Acute Toxicity Test in Animal

Paeonol of the present invention showed no side effects during administration at the dosage of 100 mg/kg, 50 times as much as 1-5 mg/kg of paeonol which was in vitro effective on radiosensitization, so it seems that paeonol is safe enough for treatment of diseases.

INDUSTRIAL APPLICABILITY

The composition of the present invention has inhibitory effects on angiogenesis, growth of solid tumor, and metastasis of tumor, and it enhances inhibition of tumor growth and survival time of patients in combination with other anti-cancer drugs. Also, the composition of the present invention can be used for the prevention and treatment of angiogenesis-related diseases such as cancer, angioma, angiofibroma, diabetic retinopathy, premature infant's retinopathy, neovascular glaucoma, corneal disease induced by angiogenesis, involution macula, macular degeneration, pterygium, retinal degeneration, retrolental fibroplasias, granular conjunctivitis, psoriasis, telangiectasis, pyogenic granuloma, seborrheic dermatitis, acne, arthritis, atherosclerosis, obesity and Alzheimer's disease.

Also, the composition of the present invention comprising paeonol for radiosensitization has superior effects on enhancing radiosensitization of various cancers in combination with radiotherapy. The combination of paeonol and irradiation can decrease viability of cancer cell, can inhibit the viability of cancer cell, and can increase survival rates and survival time of cancer patients. The combination of paeonol and lower therapeutic dosage of irradiation can show therapeutic effects of radiotherapy like using high dosage of radiation. So, the combinational treatment of irradiation and paeonol on cancer patients can decrease side effects of radiotherapy using high dosage of radiation such as damage of normal tissue, and can maximize therapeutic efficacy of radiotherapy.

As shown above, paeonol has radiosensitization-enhancing activity as well as anti-angiogenic activity, and so the composition of the present invention comprising paeonol as an active ingredient can be used, especially for treatment of angiogenesis-related disease using radiotherapy.

The invention claimed is:

1. A method for treating cancer comprising administering low-dose radiotherapy and an effective amount of paeonol or a pharmaceutically acceptable salt thereof to a subject in need of such treatment.

2. The method of claim 1, wherein the cancer is uterine cancer, lung cancer, or skin cancer.

3. The method of claim 1, wherein the paeonol or pharmaceutically acceptable salt thereof is comprised in a pharmaceutical composition in amount of 1-99 w/w %.

4. The method of claim 1, wherein the paeonol is administered before or during the radiotherapy.

5. The method of claim 1, further comprising administering an anti-cancer drug.

* * * * *